United States Patent [19]

Schoolman et al.

[11] Patent Number: 5,520,606

[45] Date of Patent: May 28, 1996

[54] MECHANICAL URINARY SPHINCTER DEVICE

[76] Inventors: Arnold Schoolman, 1000 E. 50th, Suite 310, Kansas City, Mo. 64110; Henry N. Habib, P.O. Box 1297, Osage Beach, Mo. 65066-2197

[21] Appl. No.: 76,485

[22] Filed: Jun. 14, 1993

Related U.S. Application Data

[63] Continuation of Ser. No. 599,614, Oct. 18, 1990, abandoned.

[51] Int. Cl.⁶ .................................................... A61F 2/02
[52] U.S. Cl. .................................. 600/31; 600/29; 600/30; 128/885; 128/DIG. 25
[58] Field of Search ........................... 128/DIG. 25, 885; 600/29–31

[56] References Cited

U.S. PATENT DOCUMENTS

| | | | |
|---|---|---|---|
| 2,638,093 | 5/1953 | Kulick | 600/29 |
| 3,066,667 | 12/1962 | Berry | 128/DIG. 25 |
| 3,554,184 | 1/1971 | Habib | 600/29 |
| 3,646,929 | 3/1972 | Bonnar | 600/29 |
| 3,789,828 | 2/1974 | Schulte | 128/25 |
| 3,939,821 | 2/1976 | Roth | 128/DIG. 28 |
| 4,019,498 | 4/1977 | Hawtreg et al. | 600/29 |
| 4,019,499 | 4/1977 | Fitzgerald | 128/DIG. 25 |
| 4,549,530 | 10/1985 | Finney | 600/31 |
| 4,549,531 | 10/1985 | Trick | 600/31 |
| 4,551,862 | 11/1985 | Haber | 128/DIG. 28 |
| 4,584,990 | 4/1986 | Haber et al. | 128/DIG. 25 |
| 4,587,954 | 5/1986 | Haber | 800/31 |
| 4,619,245 | 10/1986 | Haber et al. | 128/DIG. 24 |
| 4,632,114 | 12/1986 | Todd et al. | 600/31 |
| 4,846,784 | 7/1989 | Haber | 600/29 |
| 4,857,041 | 8/1989 | Annis et al. | |
| 4,875,898 | 10/1989 | Eakin | 128/DIG. 28 |
| 4,969,474 | 11/1990 | Schwarz | 600/30 |
| 4,994,020 | 2/1991 | Polyak | 600/31 |
| 5,007,894 | 4/1991 | Enhorning | 600/29 |
| 5,041,077 | 8/1991 | Kulick | 600/29 |

FOREIGN PATENT DOCUMENTS

| | | | |
|---|---|---|---|
| 3139811 | 4/1983 | Germany | 523/11 |

OTHER PUBLICATIONS

Hadley et al.; "The Treatment of Male Urinary Continence"; Campbell's *Urology*, 5th Ed.,vol. 1, Chap. 72, W. B. SAunders Co., Philadelphia, 1986, pp. 2658–2679.

Shortliffe et al.; "Urinary Incontinence in the Female"; Campbell's *Urology;* 5th Ed., vol. 1, Chap. 73, W. B. SAunders Co., Philadelphia, 1986, pp. 2680–2717.

Turner–Warwick; "Urinary Fistulae in the Female"; Campbell's *Urology,* 5th Ed., vol. 1, Chapt. 74, W. B. Saunders Co., Philadelphia, 1986, pp. 2718–2738.

*Primary Examiner*—David H. Willse
*Assistant Examiner*—K. M. Reichle
*Attorney, Agent, or Firm*—Litman, McMahon and Brown

[57] ABSTRACT

A method and apparatus for the treatment of urinary incontinence comprising the application of a compressive force to the tissue surrounding the urethra from below the urethra upwards towards the pubic bone. The apparatus comprises an inflatable, urethra-compressing balloon having a tissue-engaging surface positioned between layers of tissue adjacent the urethra on a side of the urethra opposite the pubic bone. The balloon flow communicates with a fluid reservoir secured to the frontal portion of the pubic bone. A patient having the apparatus surgically-implanted therein may selectively advance hydraulic fluid between the reservoir and the balloon so as to inflate or deflate the balloon and prevent or allow bladder emptying respectively.

4 Claims, 2 Drawing Sheets

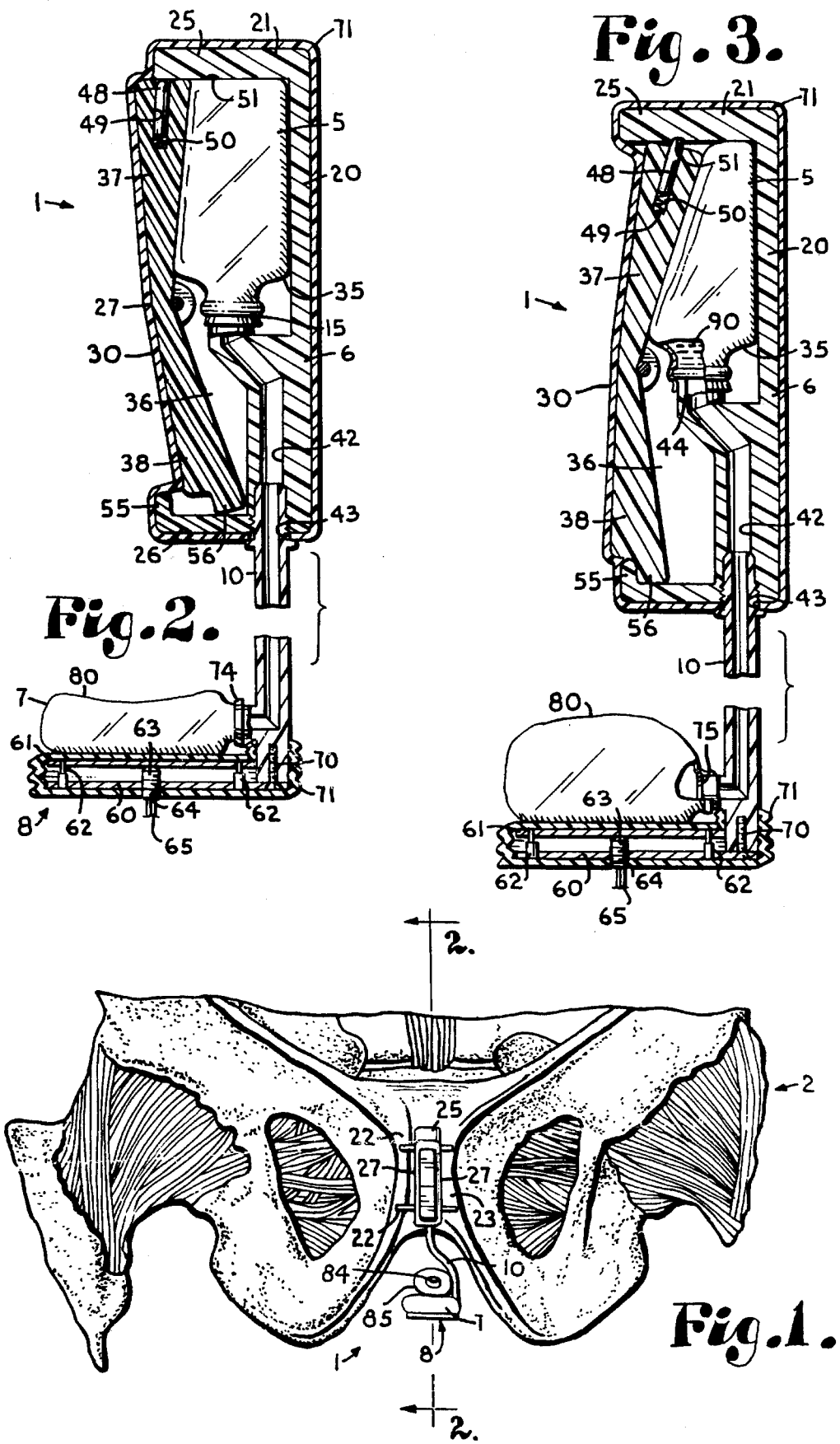

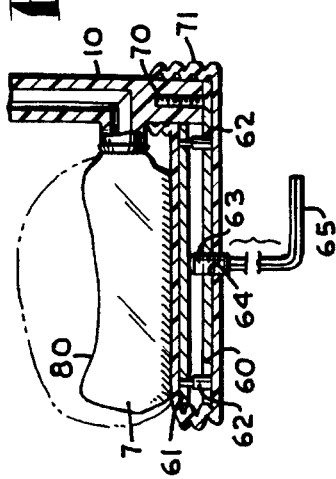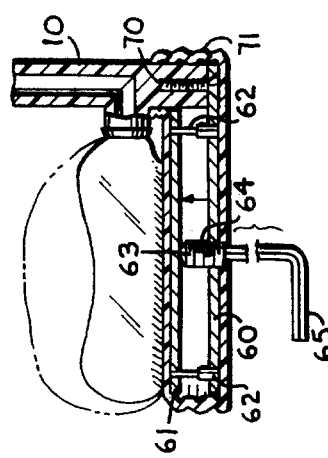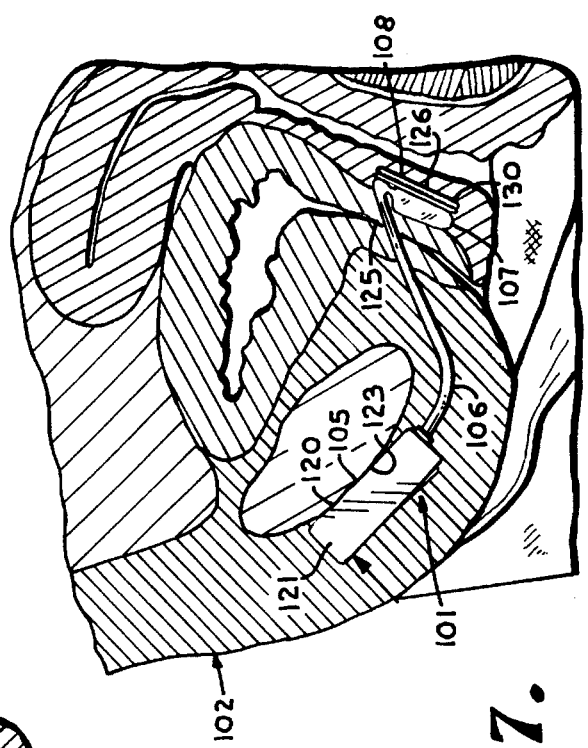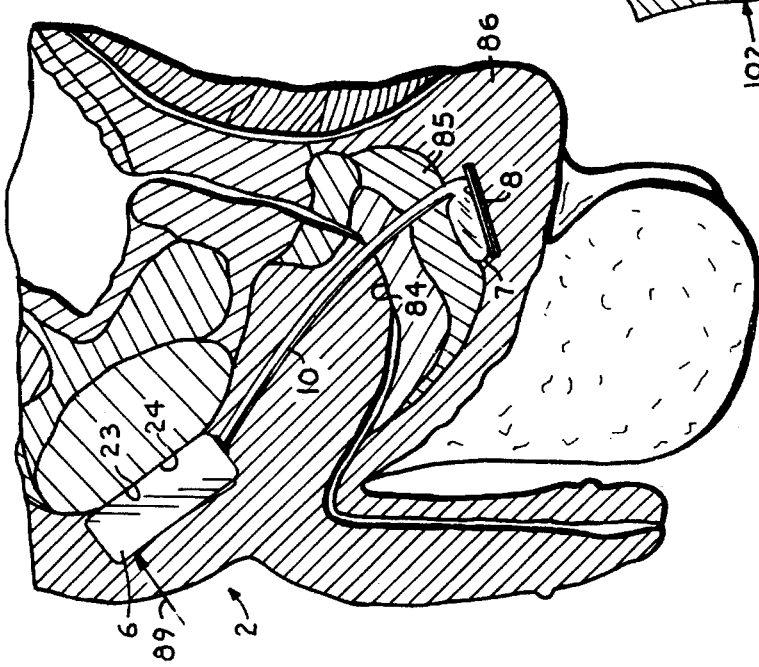

MECHANICAL URINARY SPHINCTER DEVICE

CROSS-REFERENCE TO RELATED APPLICATIONS

This application is a continuation of U.S. patent application Ser. No. 07/599,614, filed Oct. 18, 1990, and entitled MECHANICAL URINARY SPHINCTER DEVICE, now abandoned.

BACKGROUND OF THE INVENTION

The present invention relates to a method and a surgically-implanted device for providing urinary continence.

Lack of urinary sphincter control represents a major medical problem with widespread economic and social ramifications. Significant psychiatric problems frequently accompany this syndrome with the patients withdrawing from society. In addition, serious skin reactions and other hygienic difficulties result from urinary incontinence.

Incontinence may be caused by any of several factors, including: surgical scarring, severe pelvic trauma, congenital anatomic disorders, congenital or acquired neurogenic disorders, psychogenic causes, pharmacologic causes, radiotherapy to the pelvis and carcinoma of the prostrate. Various methods and devices have been developed for the treatment of incontinence. In some cases, pharmacologic agents are effective in treating incontinence. Nerve stimulation has also been found to be effective in treating some forms of incontinence. Many cases, however, require surgery either to reconstruct the urethra or to implant a prosthesis for urinary continence.

One of the more effective treatments for urinary incontinence has been the artificial, inflatable urinary sphincter. The artificial, inflatable urinary sphincter generally comprises an inflatable cuff, a fluid reservoir and a pump. The artificial sphincter is surgically implanted so that the cuff surrounds the bulbar urethra and the pump is placed in an accessible location such as the scrotum. The cuff is normally filled with fluid so as to constrict the bulbar urethra and prevent the bladder from emptying. When the user wishes to empty his or her bladder, the pump is squeezed, which forces fluid out of the cuff and into the reservoir, thereby deflating the cuff and opening the urethra.

Although effective, the artificial, inflatable urinary sphincter has some serious shortcomings. The main difficulty with such a sphincter is that the constant encircling pressure applied to the bulbar urethra results in unacceptable urethra erosion and scarring because the sphincter encircles the urethra and substantially restricts blood flow therein. After several years of use, such a sphincter may result in severe damage to the urethra.

SUMMARY OF THE INVENTION

The present invention provides a method and an apparatus for treating urinary incontinence in men and women. The method provides for the compression of the urethra through intervening, protective perineal tissue rather than scar-forming balloons or other urethral-encircling techniques. A compressive force is applied against the urethra from below the urethra so as to compress any intervening, protective perineal tissue and the urethra to prevent emptying of the bladder. The force can be selectively released and reapplied when the bladder is to be emptied.

The apparatus of the present invention comprises a surgically-implanted compressive device, preferably anchored to the pubic bone on the pelvis. The device generally comprises a fluid reservoir, a reservoir enclosure frame, an inflatable, urethra-compressing balloon and a balloon support plate assembly. The inflatable, urethra-compressing balloon is in flow communication with the fluid reservoir through a fluid transfer tube.

The fluid reservoir is maintained within the reservoir enclosure frame which is in turn secured to the frontal portion of the pubic bone. A manually-operated and pivotable compression switch extends across an upper portion of the reservoir enclosure frame such that the fluid reservoir is positioned within the reservoir enclosure frame beneath the pivotable compression switch. When an external force is manually applied to the compression plate by a user, the compression plate pivotally and compressively engages the fluid reservoir.

The balloon support plate assembly is positioned between the layers of tissue adjacent the urethra on the side of the urethra opposite the pubic bone so as to extend completely across a cross-section of the urethra. In male patients, the support plate assembly is generally positioned between the bulbo-spongiosus and adjacent perineal tissue. In female patients, the support plate assembly is generally positioned between the urethra and the vaginal wall. The balloon support plate assembly is secured to and spaced away from the reservoir enclosure frame by the fluid transfer tube.

The inflatable, urethra-compressing balloon is positioned on the balloon support plate assembly on the side closest the urethra, such that the balloon is positioned between the support plate and the urethra and the urethra is between the balloon and the pubic bone. The balloon is positioned on the support plate assembly so as to extend completely across a cross-section of the urethra.

The balloon support plate assembly is divided into an upper plate and a lower plate. The upper plate is connected to the lower plate by a plurality of telescoping arms. An adjustment screw threaded through the lower plate and engaging a lower surface of the upper plate may be threadingly advanced towards or away from the upper plate so as to advance the upper plate towards or away from the urethra, respectively, without changing the relative positioning of the lower plate. The screw may be threadingly advanced, for example, by using an Allen-type wrench.

Once the device is surgically implanted, to prevent bladder emptying, the pivotable compression switch is pivoted into a first configuration wherein the switch is in a compressing relationship with the fluid reservoir so as to urge hydraulic fluid within the reservoir to transfer through the fluid transfer tube and into the inflatable, urethra-compressing balloon under elevated pressure such that the transfer of hydraulic fluid inflates the balloon to a preselected configuration. The placement of the balloon support plate assembly causes the balloon to expand towards the pubic bone, thereby compressing the tissue, including the urethra, between the balloon and the pubic bone.

To permit bladder emptying, the pivotable compression switch is pivoted to a second position so as to be out of compressing relationship with the fluid reservoir and to allow the fluid reservoir to expand. Pressure of urine in the urethra and/or expansion of the reservoir urges the hydraulic fluid from the balloon to transfer back into the reservoir through the fluid transfer tube so as to deflate the balloon. Deflation of the balloon reduces the compressive force on the urethra so as to allow bladder emptying.

The device is surgically implanted with an Allen-type wrench operably engaging and extending from the adjustment screw in the balloon support plate assembly and extending out of the patient. After implantation surgery and after swelling has subsided, the adjustment screw may be adjusted so as to modify the relative position of the upper plate to the lower plate so as to optimize the position of the balloon thereon towards or away from the pubic bone and thereby adjust the pressure exerted on the intervening tissue when the balloon is inflated. After making these adjustments, the Allen-type wrench may be removed.

OBJECTS AND ADVANTAGES OF THE INVENTION

Therefore, the objects of the present invention are: to provide a prosthetic device for treating urinary incontinence; to provide such a device which results in minimal urethral scarring as compared to conventional urethra-encircling cuffs; to provide such a device which is readily implantable in a patient; to provide such a device which is easy to operate and reliable; to provide such a device which is effective for the treatment of incontinence in both men and women; to provide such a device which selectively prevents bladder emptying by applying a compressive force to the tissue on the side of the urethra opposite the pubis bone, wherein the force is directed towards the pubic bone so as to compress the intervening tissue, including the urethra; to provide such a device which is relatively comfortable and minimally restrictive; to provide such a device which is relatively inexpensive to manufacture and particularly well adapted for the intended usage thereof; and to provide a method of use of such a device.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of an apparatus according to the present invention positioned on a fragmentary view of the pelvic region of a user, the apparatus includes a reservoir enclosure frame secured to a frontal portion of a pubic bone of the user and an inflatable, urethra-compressing balloon inflatably engaging tissue adjacent the urethra.

FIG. 2 is an enlarged and fragmentary cross-sectional view of the apparatus, generally taken along line 2—2 of FIG. 1 with respect to the reservoir enclosure frame with the inflatable, urethra-compressing balloon shown in a generally deflated state.

FIG. 3 is a view similar to FIG. 2 showing the inflatable, urethra-compressing balloon in an inflated state.

FIG. 4 is a side elevational view of the apparatus of the present invention showing the relative positioning of the apparatus in the male pelvis which is shown in cross-section and showing the inflatable, urethra-compressing balloon in an inflated state so as to operably compress the urethra and prevent an associated bladder emptying.

FIG. 5 is a fragmentary view of the apparatus of the present invention as shown in FIG. 2, disclosing a mechanism for adjusting the positioning of the inflatable, urethra-compressing balloon.

FIG. 6 is a view similar to that of FIG. 6 showing the inflatable, urethra-compressing balloon advanced towards the urethra.

FIG. 7 is a side elevational view of the apparatus of the present invention showing the relative positioning of the apparatus in the female pelvis and showing the inflatable, urethra-compressing balloon in an inflated state so as to compress the urethra and prevent bladder emptying.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 generally represents an urethra-compressing apparatus or device in accordance with the present invention for use in treating urinary incontinence, illustrated in FIGS. 1 through 6 in conjunction with a male user 2 thereof. The device 1 generally comprises a fluid reservoir 5, a reservoir enclosure frame 6, an inflatable, urethra-compressing balloon 7 and a balloon support plate assembly 8. The fluid reservoir 5 is in flow communication with the urethra-compressing balloon 7 through fluid transfer means such as the illustrated rigid fluid transfer tube 10.

The fluid reservoir 5 is generally bulbous, having a neck 15. The reservoir 5 is made of a biasable material and filled with a nontoxic hydraulic fluid preferably saline. The reservoir 5 is maintained within the reservoir enclosure frame 6.

The reservoir enclosure frame 6 includes an elongate, rectangular base plate 20 and a wall 21 extending circumferentially therearound. In the preferred embodiment, the frame 6 is secured to a pubic bone 23 of the user 2 generally along the pubic symphysis 24 by securing means such as clamps 22 so that the base plate 20 abuts against the pubic symphysis. In this alignment, and as oriented in FIGS. 2 and 3 for purposes of directional terminology used herein, the circumferential wall 21 includes a top end wall 25, a bottom end wall 26 and opposed side walls 27 extending on either side therebetween.

A toggle switch or compression plate 30 is medially and pivotally secured to an end of each of the opposed side walls 27 opposite the base plate 20 so as to generally extend across the area defined or enclosed by the circumferential wall 21. The medial mounting of the compression plate 30 divides the space enclosed by the frame 6 and the compression plate 30 into an upper space 35 and a lower space 36, such that an upper half 37 of the compression plate extends over the upper space 35 and a lower half 38 extends over the lower space 36.

The reservoir 5 is maintained within the upper space 35 with the neck 15 directed towards the bottom end wall 26. A flow-connecting structure or conduit 42 is formed in the base plate 20 and includes an opening or tube-receiving aperture 43 extending through the bottom end wall 26 and a reservoir-connecting nipple 44 extending to the neck 15 of the reservoir 5. The neck 15 of the reservoir 5 is sealingly securable to the nipple 44 and one end of the fluid transfer tube 10 is receivable within the aperture 43 so that the fluid transfer tube 10 flow communicates with the reservoir 5.

The upper half 37 and the lower half 38 of the compression plate 30 are alternatively and selectively positionable within the upper space 35 and the lower space 36 respectively. The upper half 37 of the compression plate includes locking means such as a spring-biased locking pin 48, as shown in FIG. 2. The locking pin 48 is slidingly received within a pin-receiving aperture 49 and biased outward into abutting relationship with the top end wall 25 by a spring 50 maintained within the pin-receiving aperture 49. The top end wall 25 includes receiver means, such as illustrated dimple or depression 51, located generally medially along the inner surface of the top end wall 25 and is positioned to receive the spring-biased locking pin 48 when the upper half 37 of the compression plate 30 is advanced into the upper space 35 so that the pin 48 is aligned with the depression 51.

The reception of the spring biased locking pin 48 within the depression 51 prevents the upper half 37 of the compression plate 30 from being advanced out of the upper space 35 without the application of an additional force. The end of the pin 48, biasingly receivable by the depression 51, is rounded such that when a force is applied to the lower half 38 of the compression plate 30 directed towards the lower space 36, the resulting pivotal force directing the upper half 37 out of the upper space 35 overcomes the biasing force of the spring 50 and allows the upper half 37 of the compression plate 30 to be advanced out of the upper space 35.

The bottom end wall 26 includes a lip 55 extending along an end of the bottom end wall 26 opposite the base plate 20 and towards the top end wall 25. The lip 55 abuttingly engages an extended portion 56 of the lower half 38 of the compression plate 30 when the lower half 38 is advanced out of the lower space 36 so as to prevent the upper half 37 from being advanced past the depression 51 when the upper half 37 is advanced into the upper space 35.

The balloon support plate assembly 8 comprises a lower plate 60 and an upper plate 61 maintained in parallel and closely- spaced relation. An adjustment screw 63 is threadingly received within a threaded bore 64 centrally extending through the lower plate 60. One end of the screw 63 abuts against upper plate 61 and the other end receives a rotating tool means such as an Allen-type wrench 65. The adjustment screw 63 may be threadingly advanced or retracted within the bore 64 so as to advance the upper plate 61 towards or away from the lower plate 61.

The lower plate 61 is secured to the fluid transfer tube 10 by fastening means such as fastening screw 70. The lower plate 60, the upper plate 61 and the fastening screw 70 are all enclosed in a waterproof elastic layer 71 of a biologically-inert polymeric substance such as the product sold under the trademark "Silastic" so as to seal these structures from direct contact with body fluids and structures of the user 2. The reservoir enclosure frame 10 and the compression plate 30 are similarly enclosed in an elastic layer 71 of a biologically- inert polymeric substance.

The inflatable, urethra-compressing balloon 7 is generally bulbous and includes a neck 74. The balloon 7 is positioned on the upper plate 61 of the balloon support plate assembly 8 such that the neck 74 is secured to a balloon-receiving nipple 75 extending from the fluid transfer tube 10 and in flow communication therewith. The side of the balloon 7 opposite the upper plate 61 generally defines a tissue-engaging surface 80.

The device 1 is surgically implanted such that the base plate 20 of the reservoir enclosure frame 6 is secured to a frontal portion of the pubic bone 23 by the clamps 22 and the inflatable, urethra-compressing balloon 7 is positioned so as to engage tissue adjacent the urethra 84 of the user 2 on a side of the urethra 84 opposite the pubic bone 23. In male patients, the balloon 7 and the balloon support plate assembly 8 are positioned between the bulbo-spongiosus 85 and the adjacent perineal tissue 86, as shown in FIG. 4. The support plate assembly 8 is positioned such that the tissue-engaging surface 80 of the urethra-compressing balloon 7 engages the bulbo-spongiosus 85 on a side of the urethra 84 opposite the pubic bone 23. The tissue-engaging surface 80 extends completely across the underside of the urethra 84 as oriented in FIG. 4.

When the device 1 is inserted, the fluid transfer tube 10 is threaded or positioned around intervening tissue so as to extend to a side of the urethra 84. The tube 10 may be bent before or at the time of insertion to allow the tube 10 to achieve proper positioning of the connected support plate assembly 8 without the need to pierce adjacent tissue. However, the tube is rigid enough to prevent the tube 10 from substantially extending or contracting axially towards or away from the reservoir enclosure frame 6 during use. It is foreseen that a second tube or rigid support member(not shown) may be extended from the reservoir enclosure frame 6 to the support plate assembly 8 on the side of the urethra opposite the tube 10 to securely position the support plate assembly 8 between the bulbo-spongiosus 85 and the adjacent perineal tissue 86. Under normal intra-abdominal pressures, and with the upper half 37 of the compression plate 30 not extended into the upper space 35, the reservoir 5 rests in an expanded state generally within the entire volume of the upper space 35, and the balloon 7 rests on the upper plate 61 of the support plate assembly 8 in a nonexpanded or deflated state.

Once the device 1 is secured to the pubic bone 23, a patient may prevent bladder 88 emptying by pressing in on the external body tissue 89 adjacent to the upper half 37 of the compression plate 30 so as to advance the upper half 37 of the compression plate 30 into the upper space 35 to the position shown in FIG. 3, thereby compressing the fluid reservoir 5. As the fluid reservoir 5 is compressed, hydraulic fluid 90 is transferred from the fluid reservoir 5 to the urethra-compressing balloon 7 through the fluid transfer tube 10 so as to inflate the balloon 7 and advance the tissue-engaging surface 80 of the balloon 7 towards the pubic bone 23. The rigid positioning of the support plate assembly 8 by the rigid fluid transfer tube 10 allows the balloon to expand in one direction, generally towards the pubic bone 23. As the tissue-engaging surface 80 is advanced towards the pubic bone 23, the intervening tissue, including the urethra 84, is compressed thereby preventing bladder 88 from emptying.

As the upper half 37 of the compression plate 30 is advanced into the upper space 35 of the reservoir frame 6, the spring 50 biases the locking pin 48 against the top end wall 25 of the frame 6. When the upper half 37 of the compression plate 30 reaches the depression 51, the spring 50 biases the pin 48 into locking engagement with the depression 51. Simultaneously, the extended portion 56 of the lower half 38 of the compression plate 30 abuttingly engages the lip 55 of the bottom end wall 26 so as to fuction as a stop and prevent the upper half 37 of the compression plate 30 from extending beyond the point where the locking pin 48 biasingly engages the depression 51.

The interaction of the locking pin 48 and the depression 51 maintains the reservoir 5 in a compressed state and the balloon 7 in an inflated state, thereby compressing the urethra 88 so as to prevent the bladder 88 from emptying. When it is desired to empty the bladder 88, an external compressive force is applied to the tissue adjacent the lower half 38 of the compression plate 30 to release the locking pin 48 from the depression 51, as described above, and to advance the upper half 37 of the compression plate 30 out of the upper space 35, thereby allowing the reservoir 5 to expand to its normal resting state. The expansion of the reservoir 5 and pressure on the balloon 7 by surrounding tissue urges hydraulic fluid 90 from the balloon 7 so as to deflate the balloon 7 and remove the compressive force exerted against the intervening tissue 85 and the urethra 84. The removal of the compressive force from the urethra 84 allows the bladder 88 to empty.

The biasing force of the spring 50 is such that when pressure in the bladder 88 approaches a point where damage to the bladder 88 would occur if not reduced, the pressure exerted by the bladder 88 through the balloon 7 and the reservoir 5 against the upper half 37 of the compression plate 30 is great enough to overcome the biasing force of the spring 50, allowing the reservoir 5 to expand and the balloon 7 to deflate, thereby allowing the bladder 88 to empty. This feature prevents damage to the bladder 88 when an individual using the device is unconscious or otherwise unable to operate the device 1 to allow the emptying of the bladder 88 when needed.

The length of the tube 10 needed to properly space the support plate 8 and the urethra-compressing balloon 7 can generally be determined prior to surgery. When the device 1 is surgically implanted, the surgeon preferably leaves an adjustment tool, here the Allen-type wrench 65, in engaging relationship with the adjustment screw 63 and extending from the body of the user 2 to a position of post-operative access for the surgeon, such that, after the swelling of surgery subsides, the surgeon may adjust the pressure exerted on the urethra 84 when the balloon 7 is inflated by adjusting the spacing between the upper plate 61 and the lower plate 60. These adjustments are made using the Allen-type wrench 65, as shown in FIGS. 6 and 7.

Referring to FIG. 7, the reference numeral 101 represents an alternative embodiment of the urethra-compressing device in accordance with the present invention for use in treating female urinary incontinence shown in a female user 102. The urethra-compressing device 101 for use in treating female incontinence is substatially identical to the urethra-compressing device 1 for use in treating male incontinence and, therefore, the description of the structure will not be repeated in detail.

The urethra-compressing device 101 comprises a reservoir enclosure frame 105 with an internal fluid reservoir and a fluid transfer tube 106, an inflatable, urethra-compressing balloon 107 and a balloon support plate assembly 108. The fluid reservoir in the frame 105 is in flow communication with the balloon 107 through fluid transfer tube 106.

The reservoir enclosure frame 105 includes an elongate, rectangular base plate 120 and a wall 121 extending circumferentially therearound. The frame 105 is secured to a pubic bone 123 of the user 102 by securing means.

In female patients, the balloon 107 and the balloon support plate assembly 108 are positioned between the urethra 125 and adjacent vaginal wall tissue 126, as shown in FIG. 7. The support plate assembly 108 is positioned such that a tissue-engaging surface 130 of the balloon 107 engages the urethra 125 opposite the pubic bone 123. The tissue engaging surface 130 extends completely across a lower and rearward side of the urethra 125.

The urethra compressing device 101 operates almost identically as the urethra compressing device 1 except that when the urethra compressing balloon 107 is inflated, the tissue engaging surface 130 compressively engages the female urethra 125 instead of the bulbo-spongiosus of the male.

It is to be understood that while certain forms of the present invention have been illustrated and described herein, it is not to be limited to the specific forms or arrangement of parts described and shown. For example, the upward compressive force against the urethra could be provided by a rigid L-arm having a cross member extending between layers of tissue on the side of the urethra opposite the pubic bone where the cross member of the L-arm is mechanically advanceable towards or away from the urethra to prevent or allow bladder emptying respectively. Also, the fluid could be transferred into and out of the inflatable, urethra-compressing balloon by means of a pump.

What is claimed and desired to be secured by Letters Patent is as follows:

1. An apparatus for treating urinary incontinence comprising:
    (a) a compressible frame adapted for secure mounting to a frontal portion of a pubic bone of a user;
    (b) a rigid support member comprising an extension arm having first and second ends; said extension arm first end being attached to said compressible frame; said support member including a support plate attached to said second end of said extension arm; said support plate being positionable between layers of tissue adjacent an urethra of the user on a single side of the urethra opposite and remote from the pubic bone so as to extend completely beneath a cross-section of the urethra when said frame is mounted to the pubic bone;
    (c) an inflatable, urethra-compressible balloon positioned on a side of said support plate adapted to be closest to the urethra; said balloon having a tissue-engageable surface adapted to engage an adjacent layer of tissue on the single, opposite and remote side of the urethra and a support plate-engaging surface engaging the support plate on the side of said support plate adapted to be closest the urethra;
    (d) said extension arm having associated therewith a tube extending from a compressible fluid reservoir to said balloon;
    (e) said compressible fluid reservoir maintained within said frame and flow communicating with said balloon through said tube; said reservoir being filled with a hydraulic fluid, said fluid reservoir and said balloon cooperating so that when a compressive force is applied to said fluid reservoir, said reservoir is compressed so that said hydraulic fluid is transferred to said balloon, inflating said balloon and causing said balloon to exert force against said support plate, which is adapted to cause said tissue-engageable surface to advance towards the urethra and the pubic bone in a single direction so as to compress the urethra therebetween, thereby preventing flow of fluid through the urethra, and so that when the compressive force is removed from said reservoir, said reservoir expands back to a relaxed state thereof such that hydraulic fluid flows from said balloon into said reservoir deflating said balloon which is adapted to cause decompression of the urethra so as to allow flow of fluid through the urethra; and wherein said compressible frame comprises:
    (f) a base plate divisible into a first half and a second half; said first half receiving said reservoir;

(g) a circumferential wall extending around said base plate; and (h) a compression plate, having a compression half and a releasing half; said compression plate pivotally and medially mounted to said circumferential wall so that said compression half extends over said first half of said base plate and said releasing half extends over said second half of said base plate, said base plate, said compression plate and said fluid reservoir being positioned relative to one another in such a manner that when a compression force is applied to said compression half, said compression half advances towards said first half of said base plate and compresses said reservoir, transferring said hydraulic fluid from said reservoir to said balloon, and when a compressive force is applied to said releasing half, said releasing half advances towards said second half of said base plate and said compression half is pivotally advanced away from said first half so that said reservoir is allowed to expand so as to draw said hydraulic fluid from said balloon to said reservoir.

2. The apparatus as described in claim 1 for use in treating male urinary incontinence wherein the tissue layers comprise the bulbo-spongiosis; and (a) said tissue-engageable surface includes means for engaging the bulbo-spongiosis on the single, opposite and remote side of the urethra.

3. The apparatus as described in claim 1 and further comprising:

(a) locking means locking said compression plate in a locked position when said compression half has been advanced towards the first half of said base plate so as to maintain said reservoir in a compressed state and said balloon in an inflated state, thereby allowing extended prevention of bladder emptying; and (b) unlocking means for selectively releasing said locking means and allowing said compression plate to be advanced away from the first half of said base plate to selectively allow bladder emptying.

4. An apparatus for treating urinary incontinence comprising:

(a) a compressible frame adapted for mounting to a user;

(b) a compressible fluid reservoir maintained within said frame and flow communicating with a balloon through a tube; said reservoir being filled with a hydraulic fluid, so that when a compressive force is applied to said fluid reservoir during use, said reservoir is compressed so that said hydraulic fluid is transferred to said balloon, inflating said balloon;

(c) said balloon adapted to be positioned close to an urethra of the user so that expansion of said balloon compresses the urethra and blocks flow through the urethra so as to prevent bladder emptying;

(d) said frame comprising a base plate divisible into a first half and a second half; said first half receiving said reservoir;

(e) said frame also including a circumferential wall extending around said base plate; and (f) said frame further including a compression plate, having a compression half and a releasing half; said compression plate pivotally and medially mounted to said circumferential wall so that said compression half extends over said first half of said base plate and said releasing half extends over said second half of said base plate, said base plate, said compression plate and said fluid reservoir being positioned relative to one another in such a manner that when a compression force is applied to said compression half, said compression half advances towards said first half of said base plate and compresses said reservoir, transferring said hydraulic fluid from said reservoir to said balloon, and when a compressive force is applied to said releasing half, said releasing half advances towards said second half of said base plate and said compression half is pivotally advanced away from said first half so that said reservoir is allowed to expand so as to draw said hydraulic fluid from said balloon to said reservoir.

* * * * *